United States Patent
Williams et al.

(10) Patent No.: US 6,706,816 B2
(45) Date of Patent: Mar. 16, 2004

(54) ACCELERATOR FREE LATEX FORMULATIONS, METHODS OF MAKING SAME AND ARTICLES MADE FROM SAME

(75) Inventors: William Andrus Williams, Summerville, GA (US); Joyce Lee Cleveland, Lyerly, GA (US)

(73) Assignee: Best Manufacturing Company, Menlo, GA (US)

( * ) Notice: Subject to any disclaimer, the term of this patent is extended or adjusted under 35 U.S.C. 154(b) by 88 days.

(21) Appl. No.: 09/903,230

(22) Filed: Jul. 11, 2001

(65) Prior Publication Data

US 2003/0017286 A1 Jan. 23, 2003

(51) Int. Cl.$^7$ .................................................. C08F 8/00
(52) U.S. Cl. ........................ 525/192; 525/193; 525/194; 525/196
(58) Field of Search ............................... 525/192, 193, 525/194, 196

(56) References Cited

U.S. PATENT DOCUMENTS

| | | |
|---|---|---|
| 3,264,272 A | 8/1966 | Rees |
| 3,994,848 A | 11/1976 | Dunlop et al. |
| 4,055,530 A | 10/1977 | Poppe et al. |
| 4,307,204 A | 12/1981 | Vidal |
| 4,818,785 A * | 4/1989 | Otawa et al. ............... 524/576 |
| 4,851,463 A | 7/1989 | Opsahl et al. |
| 4,888,367 A | 12/1989 | Quigley et al. |
| 4,948,834 A | 8/1990 | Baker et al. |
| 4,997,720 A | 3/1991 | Bourbonais et al. |
| 5,014,362 A | 5/1991 | Tillotson et al. |
| 5,032,462 A | 7/1991 | Kim |
| 5,147,757 A | 9/1992 | Kurtz et al. |
| 5,179,165 A | 1/1993 | Harry, Sr. |
| 5,206,279 A | 4/1993 | Rowland et al. |
| 5,227,433 A | 7/1993 | Frankel et al. |
| 5,298,571 A | 3/1994 | Statz et al. |
| 5,314,943 A | 5/1994 | Steinwand |
| 5,387,635 A | 2/1995 | Rowland et al. |
| 5,397,833 A | 3/1995 | Arjunan |
| 5,409,971 A | 4/1995 | Wolfersberger et al. |
| 5,591,803 A | 1/1997 | Sullivan et al. |
| 5,739,196 A | 4/1998 | Jenkins et al. |
| 5,977,271 A | 11/1999 | McKay et al. |
| 5,997,969 A | 12/1999 | Gardon |
| 6,031,042 A | 2/2000 | Lipinski |

OTHER PUBLICATIONS

Neena K. Tierney and Richard A. Register, *Ion–Hopping Kinetics in Manganese–Neutralized Ethylene–Methacrylic Acid Ionomer Melts via ESR Spectroscopy*, Polymeric Materials Science and Engineering, vol. 78, 1998, American Chemical Society, pp. 200–201.

Carl J. Serman, Paul C. Painter and Michael M. Coleman, *FTIR Studies of Ethylene–co–Methacrylic Acid/Poly(Vinyl Methyl Ether) Blends Containing Zinc Ions*, Polymer Preprints, vol. 29, No. 1, Jun. 1988, American Chemical Society, pp. 315–316.

* cited by examiner

*Primary Examiner*—Nathan M. Nutter
(74) *Attorney, Agent, or Firm*—Kilpatrick Stockton LLP

(57) ABSTRACT

The present invention is directed to methods of making natural or synthetic latex articles without the use of accelerators, thiurams or carbamates. The method includes making an elastomeric material by mixing a base polymer containing carboxylate groups with a carboxylic acid or derivative thereof, a divalent or trivalent metal, an amine or amino compound, and a neutralizing agent. The elastomeric material is formed into a latex article. The present invention is also directed to a latex article made according to this method. The latex article does not contain any accelerators, thiurams or carbamates.

7 Claims, No Drawings

ACCELERATOR FREE LATEX FORMULATIONS, METHODS OF MAKING SAME AND ARTICLES MADE FROM SAME

FIELD OF THE INVENTION

The present invention relates to latex formulations that do not contain accelerators, thiurams, or carbamates, and also relates to methods of making such formulations and to articles made from such formulations.

BACKGROUND OF THE INVENTION

Thiurams, accelerators and carbamates in natural and synthetic latex articles have historically been associated with type IV chemical allergic reactions in humans. The likelihood of such reactions is lessened when the article goes through a pre-leach and post leach process. However, those people who are hypersensitive may still react to accelerators, thiurams and carbamates not extracted during the leaching process.

Producing dipped natural or synthetic latex products is labor intensive, time consuming and expensive. As a result, many producers experience lower profit margins. High scrap rates from articles being stuck together or to molds and compounding errors also contribute to increased manufacturing costs. The energy required to produce a product may fluctuate based on weather, inconsistencies in compounding and mechanical failures. This is also reflected in the quality of the finished product and profitability.

For the purposes of cost reduction and improved chemical resistance, many polymers are laminated or over dipped with other polymers. However, due to differences in physical properties and chemical structure these polymers do not adhere well to each other. Over dipped goods often delaminate easily when subjected to stress or upon aging. This creates hazards to the end user that relies upon the integrity of the films for protection. The manufacturer is also subjected to increased liability when product failure occurs. This problem is particularly applicable to the glove industry. Glove manufacturers often face increased scrap rates when the product delaminates in the stripping and post processing stages. To overcome this problem it is often necessary for the manufacturer to blend the polymers and then overdip. This increases operating cost and reduces the chemical resistance of the prevalent polymer.

SUMMARY OF THE INVENTION

The present invention solves the above-described problems by providing natural or synthetic latex formulations that do not include accelerators, thiurams or carbamates. As a result, type IV chemical allergic reactions associated with these compounds are prevented. In addition, the latex formulations of the present invention provide improved adhesion between dissimilar polymers used in latex articles. The latex formulation of the present invention comprises a base polymer comprising carboxylate groups, a carboxylic acid or derivatives thereof, a divalent or trivalent metal, an amine or amino compound, and a neutralizing agent in an amount sufficient to neutralize at least a portion of the carboxylate groups in the base polymer.

The method of the present invention includes making an elastomeric material by mixing a base polymer comprising carboxylate groups with a carboxylic acid or derivatives thereof, a divalent or trivalent metal, an amine or amino compound, and a sufficient amount of a neutralizing agent to neutralize at least a portion of the carboxylate groups in the base polymer. Without desiring to be bound by a theory of operation, it is believed that the carboxylic acid or derivatives thereof provides a level of carboxyl groups to crosslink with the base polymer and complex with the divalent or trivalent metal without the use of an accelerator, thiuram or carbamate. The elastomeric material is formed into a latex article.

More particularly, the base polymer is acrylonitrile and the carboxylic acid derivative is preferably ethylene acrylic acid. In addition, the divalent or trivalent metal is preferably zinc, preferably in the form of zinc oxide, and the neutralizing agent is preferably potassium hydroxide.

The method of the present invention is useful in producing various latex articles including gloves.

The present invention is also directed to an article made from an elastomeric material comprising a base polymer having carboxylate groups, a carboxylic acid or derivatives thereof, a divalent or trivalent metal, an amine or amino compound, and a neutralizing agent to neutralize at least a portion of the carboxylate groups in the base polymer. The carboxylic acid or derivative thereof provides a level of carboxyl groups to crosslink with the base polymer and complex with the divalent or trivalent metal. The elastomeric material does not contain an accelerator, thiuram or carbamate.

The elastomeric material is further characterized by preferably having a tensile strength from about 2000 psi to about 2500 psi, and a 500% modulus from about 400 psi to about 800 psi. In addition, the elastomeric material preferably has an elongation from about 600% to about 700%.

Other objects, features and advantages of this invention will become apparent upon reading the following detailed description in conjunction with the claims.

DESCRIPTION OF THE PREFERRED EMBODIMENTS

As summarized above, the present invention is directed to improved latex formulations and to methods of making improved latex formulations and articles made there from that do not contain thiurams, accelerators or carbamates, thereby significantly reducing type IV chemical allergic reactions normally associated with natural and synthetic latex. In addition, substantial improvements in operating efficiency are realized by the utilization of lower oven temperatures in the present invention, ease of compounding and inherent strength of the resulting article when dried.

As used herein, the term "polymer" includes homopolymers, copolymers, terpolymers and modifications thereof.

The term "tensile strength" as used herein means the energy required to stretch a material to the breaking point.

The term "elongation" as used herein means the percent stretch of a material at the breaking point.

The term "500% modulus" as used herein means the amount of energy it takes to stretch a material 500% of a predetermined length.

The present invention includes an elastomeric material formed from a latex formulation containing a base polymer. The base polymer is combined with a carboxylic acid, or derivatives thereof, a divalent or trivalent metal, an amine or amino compound and a neutralizing agent. The latex formulation is based on the dry weight of the base polymer being used. The number of carboxylate groups on the base polymer will vary with the amount of unsaturated acid groups present in the polymer. The pH of the base polymer usually varies from about 8.0 to about 8.5, with a pH of 8.4 being typical. In addition, the base polymer generally has an acid number from about 4 to about 8. Typically, the acid number of the base polymer is about 6.

Examples of suitable base polymers include, but are not limited to natural latex rubber and synthetic latex polymers, such as, acrylonitrile, butadiene rubber such as synthetic butadiene rubber and carboxylated butadiene rubber, neoprene, isoprene, polychloroprene, and copolymers, blends and mixtures thereof. Preferably, the base polymer is acrylonitrile. Suitable acrylonitrile base polymers include Reichhold 68074, Reichhold 68077, DP3040 and BP2000, all available from Reichhold of Research Triangle Park, NC. Dupont neoprene 750 or 761, available from Dupont Dow Elastomers LLC of Hockessin, Del. may also be used as the base polymer in the present invention.

A neutralizing agent is used to neutralize the carboxylate groups on the base polymer. Sufficient neutralizing agent is used such that all of the carboxylate groups or only a portion of the carboxylate groups on the base polymer may be neutralized. The latex formulation preferably contains from about 0.1 to about 1.0 part neutralizing agent based on the total dry weight of the base polymer. More preferably, the latex formulation contains from about 0.2 to about 0.7 part neutralizing agent based on the total dry weight of the base polymer. The neutralizing agent is used to adjust the pH of the base polymer to between about 8.7 and about 9.2. Desirably, the pH of the base polymer is adjusted to about 8.9. Potassium hydroxide is preferably used as the neutralizing agent. Additional neutralizing agents which may be used in the present invention include, but are not limited to, sodium hydroxide, lithium hydroxide, ammonium hydroxide, and mixtures thereof.

Carboxylic acid, or derivatives thereof, are added to the latex formulation in order to provide a known level of free carboxyl groups which can crosslink with the base polymer and complex with the divalent or trivalent metal. Prior to complexing with the divalent or trivalent metal, the carboxyl groups are preferably in a neutralized state. Any derivative of carboxylic acid may be used in the method of the present invention. However, a carboxylic acid with a functionality equal to or greater than two or a carboxylated copolymer with free carboxyl groups on the end of the polymer chain should be present to react with an amine group or amino group and complex with the divalent or trivalent metal. For example, suitable carboxylic acids, include, but are not limited to, oxalic acid, adipic acid, citric acid, malic acid, glutaric acid, pimelic acid, tartaric acid, succinic acid, malonic acid, maleic acid, fumaric acid, orthophthalic acid, isophthalic acid, terephthalic acid. Polymers, copolymers and mixtures of the foregoing carboxylic acids can also be used. Derivatives of carboxylic acid include, but are not limited to, ethylene acrylic acid copolymer, poly(acrylic acid), poly(methacrylic acid), and copolymers, blends and mixtures thereof. Desirably, ethylene acrylic acid copolymer is used in the formulation of the present invention. A suitable ethylene acrylic acid copolymer is Chemcor WE4-25A available from Chemcor of Chester, N.Y. The concentration of the carboxylic acid, or derivatives thereof, is preferably from about 0.1 to about 10 parts based on the total dry weight of the base polymer. More preferably, the concentration of the carboxylic acid, or derivatives thereof, is from about 0.2 to about 8 parts, and even more preferably from about 0.2 to about 2.0 parts based on the total dry weight of the base polymer.

As stated above, the divalent or trivalent metal used in the present invention forms a complex with the carboxylic acid compound and the base polymer. The neutralized carboxylic acid groups in the carboxylic acid compound and the base polymer interact with the divalent or trivalent metal to form ionic bonds as depicted by the following groups: —(COO)$_2$X, wherein X represents the divalent or trivalent metal. Such groups are fundamental to the crosslinked network formed in the elastomer.

The metal ion enhances the viscoelastic properties of the elastomeric material. When stretched, polymers may not always have a fully elastic response. This response may be combined with irreversible deformations, i.e. viscous flow. Hence the phenomenon becomes viscoelastic, which refers to the time-dependent flow within the material. This is observable by a delayed response to an applied stress, also known as time relaxation. When ionic groups are added to a polymer, the viscosity of the polymer is increased and the relaxation time of the ionomer is affected. Without being bound to a theory of operation, in the present invention, it is believed that the metal forms a non-static ionic bond with the base polymer and the carboxylic acid compound. In other words a "hopping" relaxation mechanism is thought to be produced, whereby re-ordering of ionic crosslinks takes place along with some internal flow within the ionomer chains.

Any divalent or trivalent metal ion capable of complexing with the base polymer and carboxylic acid compound may be used in the present invention. A preferred metal ion is zinc$^{+2}$ in the form of the compound zinc oxide. Other suitable divalent or trivalent metal ions include but are not limited to zinc from zinc ammonium carbonate, titanium from titanium dioxide, aluminum from aluminum oxide, manganese from manganese oxide, copper, nickel, and mixtures thereof. The concentration of the divalent or trivalent metal compound in the latex formulation is preferably from about 0.1 to about 5 parts based on the total dry weight of the base polymer. More preferably, the concentration of the divalent or trivalent metal is from about 0.3 to about 2 parts based on the total dry weight of the base polymer.

An amine or amino compound is used to solubilize the divalent or trivalent metal in the latex formulation by adjusting the pH of the latex formulation. Preferably, the amine or amino compound adjusts the pH of the latex formulation to between about 8 and 10. More preferably, the amine or amino compound adjusts the pH of the latex formulation to between about 9.2 and 9.8. Any amine or amino compound capable of adjusting the pH of the latex formulation to the required level may be used in the present invention. Examples of suitable amine and amino compounds include, but are not limited to aliphatic primary amines, alkanoamines, and mixtures thereof. Preferably the amine or amino compound is ammonium hydroxide.

The latex formulation may also include additives commonly used to make latex articles, such as processing agents, pH control agents, coagulants, and colorants. As will be appreciated by those skilled in the art, the amounts of these additives may be varied considerably.

The latex article formed from the elastomeric material may be straight dipped, coagulant dipped, cast or coated depending on the item being produced. The article may be air-dried or oven dried at low to high temperatures depending upon the desired production time and preferred quality. However, higher temperatures around 212° F. typically produce cosmetic defects such as cracks, blisters and water spots on the resulting latex film. The preferred drying temperature is from about 140° F. to about 250° F. More preferably, the drying temperature of the latex article is from about 160° F. to about 200° F., and even more preferably the drying temperature is about 180° F. As the latex formulation of the present invention contains no accelerators and utilizes an acid-base reaction, additional heat is not needed after the film is dry to produce an article with adequate physical properties. Thus, the method of the present invention provides a means of utilizing low oven temperatures to achieve the same results as higher oven temperatures needed for traditional curing systems in current natural and synthetic latex formulations.

The method of the present invention also improves adhesion between dissimilar polymers. This is particularly useful in the formation of latex articles which are laminated or over dipped using a compound containing a dissimilar polymer. The method of the present invention prevents delamination in such products. For example, adhesion is improved between acrylonitrile butadiene and polychloroprene or natural rubber, as well as between carboxylated and non-carboxylated polymers. Furthermore, the method of the present invention reduces odors associated with the use of accelerators, thiurams and carbamates. It should also be noted that the latex formulation may be pre-compounded and shipped in a liquid state.

The elastomeric material of the present invention is characterized by being substantially impermeable to water vapor and liquid water, having a relatively high tensile strength, and having a relatively low resilience. The elastomeric material is useful in articles such as gloves suitable for medical, clean room and industrial applications in which natural and synthetic latexes are used, condoms, tubing, catheters, bladder bags, balloons, finger cots, coated fabrics, rubber bands, tourniquets, elastic bands, diaphragms, dental dams, paints, sheaths, and clean room articles. If desirable, the articles of the present invention may be thin walled. These properties are particularly useful in latex coverings, and even more particularly useful in gloves.

The elastomeric material of the present invention was found to have the following properties as measured according to ASTM D-412 on a sample of material having a thickness from about 4.0 to about 4.5 mils. The material has a tensile strength from about 1800 psi to about 4000 psi. Preferably, the material has a tensile strength from about 2000 psi to about 2500 psi. The elastomeric material of the present invention has an elongation from about 500% to about 800%, and preferably from about 600% to about 700%. In addition, the elastomeric material has a 500% modulus from about 350 psi to about 2000 psi, and preferably, the elastomeric material has a 500% modulus from about 400 psi to about 800 psi.

As previously mentioned, the accelerator free material of the present invention prevents type IV chemical allergic reactions related to the use of thiurams, accelerators, and carbamates in latex and synthetic latex. In addition, the high level of strength as illustrated by the above described properties, enables the elastomeric material and articles made there from to be pulled and stretched a considerable amount before breaking. Thus, a glove made with the elastomeric material of the present invention can fit closely to the wearer's skin because it can be pulled with a considerable amount of force when being donned by the wearer. This is particularly important for surgical gloves which must be thin and fit closely.

Furthermore, gloves made with the elastomeric material of the present invention are particularly useful as surgical gloves because they relax on the hands of the wearer after being donned so that there is little resistance to movement by the wearer's fingers and there is little restriction of blood vessels in the wearer's hands. Thus, gloves produced from the elastomeric material of the present invention can be worn for extended periods of time without tiring or numbing the hands of the wearer, thereby giving the wearer greater comfort and greater sensitivity in performing delicate tasks.

The present invention is further illustrated by the following examples which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Latex gloves were made as follows. A latex formulation having the formula set forth in Table 1 was thoroughly mixed in a container. The amount of each component of the material is set forth based upon 100 dry parts by weight of the base polymer. Table 1 shows the amount of acrylonitrile present in the latex formulation, however, the acrylonitrile was added to the latex formulation as a latex comprising 40% by weight of acrylonitrile with the remainder water and surfactants. The titanium dioxide is used to add opacity to the elastomeric material. The Chemcor 369C is used as an antiozonant and is available from Chemcor, of Chester, N.Y. Additional suitable antiozonants include but are not limited to Michemlube 182 available from Michelman Inc. of Cincinnati, Ohio, and other carnuaba and paraffin wax blends. Water was added to the latex formulation to produce a formulation containing 25% solids. Total solids in the latex formulation of the present invention are between about 20% and 30% for a 4–8 mil dipped product.

Three glove forms were prepared by washing with a detergent and rinsing. The glove forms were then dipped in a coagulant mixture comprising calcium nitrate, water and a nonionic soap to promote congealing of the latex around the glove forms. After being dipped in the coagulant mixture, the glove forms were dipped in the latex material. The latex coated glove forms were then dipped in a leach consisting of warm water and then into a powder slurry consisting of powdered starch. The latex coated glove forms were then placed in an oven for 30 minutes at 180° F. to dry the latex coating on the glove forms. After removal from the oven, the glove forms were dipped in a leach consisting of warm water. The latex gloves were then stripped from the glove forms and tumbled.

TABLE 1

| EXAMPLE 1 LATEX FORMULATION | |
|---|---|
| Acrylonitrile (Reichhold 68073) | 100 |
| Potassium Hydroxide | 0.4 |
| Ethylene acrylic acid (Chemcor WE4-25A) | 0.3 |
| Zinc Oxide | 0.3 |
| Titanium Dioxide | 3.4 |
| Chemcor 369C (antiozonant) | 2.2 |
| Blue pigment | .072 |
| Ammonia Hydroxide | to pH 9.3 |
| Water | to 25% total solids |

The tensile strength, elongation, and 500% modulus of the gloves made according to Example 1 were each tested using ASTM D-412. The above procedure was repeated approximately 30 times so that 100 glove forms were tested. The results of these tests are shown in Table 2.

TABLE 2

| ASTM D-412 Physical Properties | |
| --- | --- |
| | Range |
| Thickness | 4.8 mil |
| Tensile Strength | 1800–4000 psi |
| 500% Modulus | 350–2000 psi |
| Elongation @ Break | 500–800 psi |

An alternative latex formulation for use in the present invention may be formed by using the latex formulation set forth in Table 1 and substituting Dupont neoprene 750 for the acrylonitrile.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. An elastomeric material comprising:

a base polymer;

a carboxylic acid or a derivative thereof;

a compound including a divalent or trivalent metal;

an amine or amino compound; and a neutralizing agent to neutralize at least a portion of the carboxylate groups in the base polymer;

wherein the carboxylic acid or derivative thereof provides a level of carboxyl groups sufficient to crosslink with the base polymer and to complex with the divalent or trivalent metal, and wherein the elastomeric material does not comprise an accelerator, thiuram or carbamate.

2. The elastomeric material of claim 1, wherein the elastomeric material has a tensile strength from about 1800 psi to about 4000 psi.

3. The elastomeric material of claim 1, wherein the elastomeric material has a tensile strength from about 2000 psi to about 2500 psi.

4. The elastomeric material of claim 1, wherein the elastomeric material has a 500% modulus from about 350 psi to about 2000 psi.

5. The elastomeric material of claim 1, wherein the elastomeric material has a 500% modulus from about 400 psi to about 800 psi.

6. The elastomeric material of claim 1, wherein the elastomeric material has an elongation from about 500 psi to about 800 psi.

7. The elastomeric material of claim 1, wherein the elastomeric material has an elongation from about 600 psi to about 700 psi.

* * * * *